(12) United States Patent
Prisco

(10) Patent No.: US 10,772,690 B2
(45) Date of Patent: Sep. 15, 2020

(54) PASSIVE PRELOAD AND CAPSTAN DRIVE FOR SURGICAL INSTRUMENTS

(71) Applicant: INTUITIVE SURGICAL OPERATIONS, INC., Sunnyvale, CA (US)

(72) Inventor: Giuseppe Maria Prisco, Calci Pisa (IT)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 33 days.

(21) Appl. No.: 16/026,673

(22) Filed: Jul. 3, 2018

(65) Prior Publication Data

US 2018/0311001 A1    Nov. 1, 2018

Related U.S. Application Data

(63) Continuation of application No. 15/001,948, filed on Jan. 20, 2016, now Pat. No. 10,022,194, which is a
(Continued)

(51) Int. Cl.
*A61B 34/30* (2016.01)
*B25J 9/10* (2006.01)
(Continued)

(52) U.S. Cl.
CPC .............. *A61B 34/30* (2016.02); *A61B 34/37* (2016.02); *A61B 34/71* (2016.02); *B25J 9/1045* (2013.01);
(Continued)

(58) Field of Classification Search
CPC .. A61B 2017/00477; A61B 2034/2061; A61B 2034/302; A61B 2034/305;
(Continued)

(56) References Cited

U.S. PATENT DOCUMENTS

| 793,510 A | 6/1905 | Cramer et al. |
|---|---|---|
| 4,117,359 A | 9/1978 | Wehde |

(Continued)

FOREIGN PATENT DOCUMENTS

| CN | 1127332 A | 7/1996 |
|---|---|---|
| CN | 2573759 Y | 9/2003 |

(Continued)

OTHER PUBLICATIONS

International Search Report and Written Opinion for Application No. PCT/US14/050838, dated Nov. 25, 2014, 11 pages (Continued)

*Primary Examiner* — Ahmed M Farah
*Assistant Examiner* — Jonathan T Kuo
(74) *Attorney, Agent, or Firm* — Haynes and Boone, LLP.

(57) ABSTRACT

A system comprises a medical instrument including a rotatable capstan. The rotatable capstan includes a capstan coupling member that can engage with a drive shaft coupling member such that rotation of the drive shaft causes rotation of the capstan about a drive axis concentric with the drive shaft, and can disengage from the drive shaft coupling member such that rotation of the drive shaft does not cause rotation of the capstan.

20 Claims, 4 Drawing Sheets

Related U.S. Application Data continuation of application No. 12/286,644, filed on Sep. 30, 2008, now Pat. No. 9,259,274.

(51) Int. Cl.
  *A61B 34/00* (2016.01)
  *A61B 34/37* (2016.01)
  *A61B 17/00* (2006.01)
  *A61B 34/20* (2016.01)

(52) U.S. Cl.
  CPC ............ *A61B 2017/00477* (2013.01); *A61B 2034/2061* (2016.02); *A61B 2034/302* (2016.02); *A61B 2034/305* (2016.02); *A61B 2034/715* (2016.02)

(58) Field of Classification Search
  CPC ... A61B 2034/715; A61B 34/37; A61B 34/71; A61B 34/30–37; B25J 9/1045
  See application file for complete search history.

(56) References Cited

U.S. PATENT DOCUMENTS

| | | | |
|---|---|---|---|
| 4,259,876 A | 4/1981 | Belyanin et al. | |
| 4,281,447 A | 8/1981 | Miller et al. | |
| 4,283,165 A | 8/1981 | Vertut | |
| 4,899,608 A | 2/1990 | Knappe et al. | |
| 5,269,031 A * | 12/1993 | Alexander | A47C 20/041 |
| | | | 192/48.2 |
| 5,373,317 A | 12/1994 | Salvati et al. | |
| 5,555,897 A | 9/1996 | Lathrop, Jr. et al. | |
| 5,624,398 A | 4/1997 | Smith et al. | |
| 5,674,024 A | 10/1997 | Daumal et al. | |
| 5,784,542 A | 7/1998 | Ohm et al. | |
| 5,792,135 A | 8/1998 | Madhani et al. | |
| 5,824,007 A | 10/1998 | Faraz et al. | |
| 6,007,550 A | 12/1999 | Wang et al. | |
| 6,102,850 A | 8/2000 | Wang et al. | |
| 6,132,368 A | 10/2000 | Cooper | |
| 6,139,245 A | 10/2000 | Hofmeister | |
| 6,246,200 B1 | 6/2001 | Blumenkranz et al. | |
| 6,331,181 B1 | 12/2001 | Tierney et al. | |
| 6,371,952 B1 | 4/2002 | Madhani et al. | |
| 6,394,998 B1 | 5/2002 | Wallace et al. | |
| 6,459,926 B1 | 10/2002 | Nowlin et al. | |
| 6,491,701 B2 | 12/2002 | Tierney et al. | |
| 6,494,662 B1 | 12/2002 | De | |
| 6,496,099 B2 | 12/2002 | Wang et al. | |
| 6,522,906 B1 | 2/2003 | Salisbury, Jr. et al. | |
| 6,800,056 B2 | 10/2004 | Tartaglia et al. | |
| 6,817,974 B2 | 11/2004 | Cooper et al. | |
| 6,974,411 B2 | 12/2005 | Belson | |
| 6,984,203 B2 | 1/2006 | Tartaglia et al. | |
| 6,994,708 B2 | 2/2006 | Manzo | |
| 6,997,079 B2 | 2/2006 | Nomura et al. | |
| 7,048,745 B2 | 5/2006 | Tierney et al. | |
| 7,118,582 B1 | 10/2006 | Wang et al. | |
| 7,261,726 B2 | 8/2007 | Jinno et al. | |
| 7,316,681 B2 | 1/2008 | Madhani et al. | |
| 7,331,967 B2 | 2/2008 | Lee et al. | |
| 7,524,320 B2 | 4/2009 | Tierney et al. | |
| 7,666,191 B2 | 2/2010 | Orban, III | |
| 7,699,855 B2 | 4/2010 | Anderson et al. | |
| 7,727,244 B2 | 6/2010 | Orban, III et al. | |
| 7,823,330 B2 | 11/2010 | Ostrowski et al. | |
| 7,886,743 B2 | 2/2011 | Cooper et al. | |
| 7,901,348 B2 | 3/2011 | Soper et al. | |
| 7,930,065 B2 | 4/2011 | Larkin et al. | |
| 7,935,130 B2 | 5/2011 | Williams et al. | |
| 7,947,050 B2 | 5/2011 | Lee et al. | |
| 7,947,051 B2 | 5/2011 | Lee et al. | |
| 7,963,913 B2 | 6/2011 | Devengenzo et al. | |
| 8,142,447 B2 | 3/2012 | Cooper et al. | |
| 8,333,755 B2 | 12/2012 | Cooper et al. | |
| 8,337,397 B2 | 12/2012 | Prisco et al. | |
| 8,348,931 B2 | 1/2013 | Cooper et al. | |
| 8,444,631 B2 | 5/2013 | Yeung et al. | |
| 8,479,969 B2 | 7/2013 | Shelton, IV et al. | |
| 8,506,555 B2 | 8/2013 | Ruiz | |
| 8,551,115 B2 | 10/2013 | Steger et al. | |
| 8,620,473 B2 | 12/2013 | Diolaiti et al. | |
| 8,644,988 B2 | 2/2014 | Prisco et al. | |
| 8,771,270 B2 | 7/2014 | Burbank | |
| 8,800,838 B2 | 8/2014 | Shelton, IV et al. | |
| 8,801,601 B2 | 8/2014 | Prisco et al. | |
| 8,911,471 B2 | 12/2014 | Spivey et al. | |
| 9,028,494 B2 | 5/2015 | Shelton, IV et al. | |
| 9,078,684 B2 | 7/2015 | Williams | |
| 9,121,494 B2 | 9/2015 | Buchleitner | |
| 9,204,923 B2 | 12/2015 | Manzo et al. | |
| 9,232,979 B2 | 1/2016 | Parihar et al. | |
| 9,259,274 B2 | 2/2016 | Prisco | |
| 9,291,793 B2 | 3/2016 | Cooper | |
| 9,339,342 B2 | 5/2016 | Prisco et al. | |
| 9,387,048 B2 | 7/2016 | Donhowe et al. | |
| 9,452,276 B2 | 9/2016 | Duindam et al. | |
| 9,533,122 B2 | 1/2017 | Weitzner et al. | |
| 9,687,312 B2 | 6/2017 | Dachs, II et al. | |
| 9,757,149 B2 | 9/2017 | Cooper et al. | |
| 1,001,624 A1 | 7/2018 | Cooper et al. | |
| 1,002,219 A1 | 7/2018 | Cooper et al. | |
| 10,022,194 B2 | 7/2018 | Prisco et al. | |
| 10,130,366 B2 | 11/2018 | Shelton, IV et al. | |
| 10,238,837 B2 | 3/2019 | Duindam et al. | |
| 10,478,163 B2 | 11/2019 | Prisco et al. | |
| 2002/0087048 A1 | 7/2002 | Brock et al. | |
| 2002/0096885 A1 | 7/2002 | Gomez et al. | |
| 2002/0111635 A1 | 8/2002 | Jensen et al. | |
| 2002/0153221 A1 | 10/2002 | Schnepf | |
| 2004/0035243 A1 | 2/2004 | Duval | |
| 2005/0042943 A1 | 2/2005 | Mocivnik et al. | |
| 2005/0089345 A1 | 4/2005 | Yasumoto et al. | |
| 2005/0277875 A1 | 12/2005 | Selkee | |
| 2006/0084945 A1 | 4/2006 | Moll et al. | |
| 2007/0043338 A1 | 2/2007 | Moll et al. | |
| 2007/0137371 A1 | 6/2007 | Devengenzo et al. | |
| 2007/0156019 A1 | 7/2007 | Larkin et al. | |
| 2007/0156122 A1 | 7/2007 | Cooper et al. | |
| 2007/0232858 A1 | 10/2007 | MacNamara et al. | |
| 2007/0287992 A1 | 12/2007 | Diolaiti et al. | |
| 2008/0004603 A1 | 1/2008 | Larkin et al. | |
| 2008/0046122 A1 | 2/2008 | Manzo et al. | |
| 2008/0065102 A1 | 3/2008 | Cooper | |
| 2008/0065105 A1 | 3/2008 | Larkin et al. | |
| 2008/0087871 A1 | 4/2008 | Schena | |
| 2008/0103491 A1 | 5/2008 | Omori et al. | |
| 2008/0196533 A1 | 8/2008 | Bergamasco et al. | |
| 2009/0000899 A1 | 1/2009 | Paterra et al. | |
| 2009/0062813 A1 | 3/2009 | Prisco et al. | |
| 2009/0088774 A1 | 4/2009 | Swarup et al. | |
| 2009/0227861 A1 | 9/2009 | Ganatra et al. | |
| 2009/0324161 A1 | 12/2009 | Prisco | |
| 2010/0011900 A1 | 1/2010 | Burbank | |
| 2010/0170519 A1 | 7/2010 | Romo et al. | |
| 2010/0175701 A1 | 7/2010 | Reis et al. | |
| 2010/0318101 A1 | 12/2010 | Choi | |
| 2011/0015650 A1 | 1/2011 | Choi et al. | |
| 2011/0118754 A1 | 5/2011 | Dachs, II et al. | |
| 2011/0160743 A1 | 6/2011 | Espinal | |
| 2011/0213383 A1 | 9/2011 | Lee et al. | |
| 2011/0277775 A1 | 11/2011 | Holop et al. | |
| 2011/0282356 A1 | 11/2011 | Solomon et al. | |
| 2011/0282357 A1 | 11/2011 | Rogers et al. | |
| 2011/0282359 A1 | 11/2011 | Duval | |
| 2011/0295269 A1 | 12/2011 | Swensgard et al. | |
| 2011/0295270 A1 | 12/2011 | Giordano et al. | |
| 2012/0021867 A1 | 1/2012 | Rosmarin | |
| 2012/0111136 A1 | 5/2012 | Kawakami | |
| 2012/0118917 A1 | 5/2012 | Naughton et al. | |
| 2012/0123441 A1 | 5/2012 | Au et al. | |
| 2012/0239060 A1 | 9/2012 | Orban, III | |
| 2012/0245596 A1 | 9/2012 | Meenink et al. | |
| 2012/0289974 A1 | 11/2012 | Rogers et al. | |

(56) References Cited

U.S. PATENT DOCUMENTS

| | | |
|---|---|---|
| 2013/0096385 A1 | 4/2013 | Fenech et al. |
| 2014/0005678 A1 | 1/2014 | Shelton, IV et al. |
| 2014/0100558 A1 | 4/2014 | Schmitz et al. |
| 2015/0008090 A1 | 1/2015 | Adamczak et al. |
| 2015/0150635 A1 | 6/2015 | Kilroy et al. |
| 2015/0157355 A1 | 6/2015 | Price et al. |
| 2016/0184034 A1 | 6/2016 | Holop et al. |
| 2016/0184036 A1 | 6/2016 | Solomon et al. |
| 2016/0184037 A1 | 6/2016 | Cooper et al. |
| 2016/0199138 A1 | 7/2016 | Cooper et al. |
| 2016/0310115 A1 | 10/2016 | Prisco, Sr. et al. |
| 2016/0361049 A1 | 12/2016 | Dachs, II et al. |
| 2017/0000984 A1 | 1/2017 | Duindam et al. |
| 2017/0165017 A1 | 6/2017 | Chaplin et al. |

FOREIGN PATENT DOCUMENTS

| | | |
|---|---|---|
| CN | 2626684 Y | 7/2004 |
| CN | 1650117 A | 8/2005 |
| CN | 1763638 A | 4/2006 |
| CN | 102014759 A | 4/2011 |
| EP | 0688538 A1 | 12/1995 |
| JP | H06114000 A | 4/1994 |
| JP | H10249777 A | 9/1998 |
| JP | 2002200091 A | 7/2002 |
| JP | 2003024336 A | 1/2003 |
| JP | 2004105451 A | 4/2004 |
| JP | 2005288590 A | 10/2005 |
| JP | 2006061364 A | 3/2006 |
| JP | 2007229906 A | 9/2007 |
| JP | 2008104854 A | 5/2008 |
| JP | 2010220955 A | 10/2010 |
| WO | WO-9501757 A1 | 1/1995 |
| WO | WO-9729690 A1 | 8/1997 |
| WO | WO-2005039835 A1 | 5/2005 |
| WO | WO-2007075864 A1 | 7/2007 |
| WO | WO-2007136783 A2 | 11/2007 |
| WO | WO-2010039387 A1 | 4/2010 |
| WO | WO-2011037394 A2 | 3/2011 |
| WO | WO-2015142290 A1 | 9/2015 |

OTHER PUBLICATIONS

International Search Report and Written Opinion for Application No. PCT/US14/50957, dated Nov. 21, 2014, 11 pages.
International Search Report and Written Opinion for Application No. PCT/US14/51001, dated Nov. 20, 2014, 11 pages.
International Search Report and Written Opinion for Application No. PCT/US14/51074, dated Nov. 20, 2014, 13 pages.
International Search Report and Written Opinion for Application No. PCT/US2014/051033, dated Nov. 19, 2014, 9 pages.
International Search Report and Written Opinion for Application No. PCT/US2014/051050, dated Nov. 25, 2014, 14 pages.
Extended European Search Report for Application No. 14836283.3, dated Sep. 4, 2017, 11 pages.
Extended European Search Report for Application No. 14836336.9, dated Jun. 16, 2017, 9 pages.
Extended European Search Report for Application No. 14836512.5, dated Aug. 3, 2017, 13 pages.
Extended European Search Report for Application No. 14836696.6, dated Jun. 16, 2017, 9 pages.
Extended European Search Report for Application No. 14836832.7, dated Jun. 9, 2017, 8 pages.
Extended European Search Report for Application No. EP14836874.9, dated Mar. 17, 2017, 10 pages.
Partial Supplementary European Search Report for Application No. EP14836283.3, dated May 17, 2017, 12 pages.
Decision of Final Rejection for Korean Application No. 10-2013-7032821, dated Jul. 3, 2019, 6 pages.
Notice of Dismissal of Amendment for Korean Application No. 10-2013-7032821, dated Jul. 3, 2019, 7 pages.
Final Action dated Apr. 8, 2019 for Korean Application No. 10-2013-7032821 filed May 10, 2012, 11 pages.
Office Action dated Sep. 7, 2018 for Korean Application No. 10-2013-7032821 filed May 10, 2012, 16 pages.
International Search Report and Written Opinion for Application No. PCT/US2012/037269, dated Sep. 19, 2012, 10 pages.
Office Action dated Dec. 26, 2014 for Japanese Application No. 20140021913 filed Feb. 7, 2008, 10 pages.
Office Action dated Sep. 30, 2015 for Japanese Application No. 20140021913 filed Feb. 7, 2008, 7 pages.
PCT/US09/55727 International Search Report and Written Opinion of the International Searching Authority, dated Feb. 3, 2010, 9 pages.
Office Action dated Nov. 30, 2016 for Chinese Application No. 201510185999.6 filed Sep. 2, 2009, 24 pages.
Office Action dated Jun. 22, 2017 for Japanese Application No. 2016177316 filed Sep. 12, 2016, 7 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18184785.6, dated Nov. 23, 2018, 6 pages.
Amended Joint Claim Construction Chart, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Document 123-1, Nov. 13, 2019, 31 pages.
Amended Joint Claim Construction Chart, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Document 81, Aug. 29, 2019, 29 pages.
Auris Health, Inc.'s Opposition to Motion for Reargument Regarding Mar. 11, 2019 Scheduling Order, United States District Court for the District of Delaware, Plaintiffs: *Intuitive Surgical, Inc. and Intuitive Surgical Operations, Inc.*, V. Defendant: *Auris Health, Inc*, Jury Trial Demanded, Case No. 18-1359-MN, Document 52, Mar. 29, 2019, 8 pages.
Boehm D.H.,0et al., "Early Experience with Robotic Technology for Coronary Artery Surgery," The Annals of Thoracic Surgery, 1999, vol. 68 (4), pp. 1542-1546.
Charles, Steve et al., "Dexterity-enhanced Telerobotic Microsurgery," 1997, pp. 5-10, IEEE.
Complaint for Patent Infringement, United States District Court for the District of Delaware, Plaintiffs: *Intuitive Surgical, Inc. and Intuitive Surgical Operations, Inc.*, V. Defendant: *Auris Health, Inc*, Demand for Jury Trial, Aug. 31, 2018, 14 pages.
Da Vinci by Intuitive, Enabling Surgical Care to get Patients Back to what Matters, Case 1:18-cv-01359-MN, Document 114-1, Aug. 29, 2019, Retrieved from the Internet: URL: [https://wvvw.intuitive.com/en-us/products-and-services/da-vinci], pp. 202 pages.
Das H., et al., "Evaluation of a Telerobotic System to Assist Surgeons to Microsurgery," Computer Aided Surgery, 1999, vol. 4 (1). pp. 15-25.
Decision on Granting Institution of Inter Parties Review 35 U.S.C. 314, dated Mar. 4, 2020 for U.S. Pat. No. 6,491,701 B2, IPR2019-01532, Before Ulrike W. Jenks, Tina E. Hulse, and James A. Worth, Administrative Patent Judges., 18 pages.
Declaration of Dr, William Cimino Regarding U.S. Pat. No. 6,491,701, Petitioner: *Auris Health, Inc v. Patent Owner. Intuitive Surgical Operations, Inc.*, IPR2019- 01532, Aug. 28, 2019, 95 pages.
Declaration of Kelly E. Farnan in Support of Auris Health, Inc.'s Opposition to Motion for Reargument Regarding Mar. 11, 2019 Scheduling Order, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Document 53, 2019, 3 pages.
Declaration of Laura E. Miller in Support of Plaintiffs' Opposition to Defendant's Motion to Stay, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Exhibit, Document 122, Nov. 13, 2019, 50 pages.

(56) References Cited

OTHER PUBLICATIONS

Declaration of Shaelyn K. Dawson in Support of Defendant Auris Health, Inc.'s Motion to Stay Case Pending Inter Partes Review, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Document 119, 2019, 3 pages.

Declaration of Shaelyn K. Dawson in Support of Defendant Auris Health, Inc.'s Reply in Support of Its Motion to Stay Case Pending Inter Partes Review, United States District Court for the District of Delaware, Plaintiffs: *Intuitive Surgical, Inc. and Intuitive Surgical Operations, Inc.*, V. Defendant: *Auris Health, Inc*, Case No. 1:18-cv-01359-MN, Document 127, 2019, 2 pages.

Declaration of Taylor Patton in Support of Plaintiffs Intuitive Surgical, Inc. and Intuitive Surgical Operations, Inc.'s Opposition to Defendant Auris Health, Inc.'s Motion to Transfer, United States District Court for the District of Delaware, Plaintiffs: *Intuitive Surgical, Inc. and Intuitive Surgical Operations, Inc.*, V. Defendant: *Auris Health, Inc*, Redacted—Public Version, C.A. No. 18-1359-MN, Document 30, Dec. 11, 2018, 15 pages.

Declaration of Vera Ranieri in Support of Plaintiffs Intuitive Surgical, Inc. and Intuitive Surgical Operations, Inc.'s Opposition to Defendant Auris Health, Inc.'s Motion to Transfer, United States District Court for the District of Delaware, Plaintiffs: *Intuitive Surgical, Inc. and Intuitive Surgical Operations, Inc.*, V. Defendant: *Auris Health, Inc*, Case No. 1:18-cv-01359-MN, Document 28, Demand for Jury Trial, 2018, 4 pages.

Defendant Auris Health, Inc.'s Answer to Plaintiffs' Complaint for Patent Infringement, United States District Court for the District of Delaware, Plaintiffs: *Intuitive Surgical, Inc. and Intuitive Surgical Operations, Inc.*, V. Defendant: *Auris Health, Inc*, Case No. 18-1359-LPS, Jury Trial Demanded, Document 12, Oct. 25, 2018, 12 pages.

Defendant Auris Health, Inc.'s Opening Brief in Support of Its Motion to Stay Case Pending Inter Partes Review, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Jury Trial Demanded, Document 118, Oct. 30, 2019, 18 pages.

Defendant Auris Health, Inc.'s Reply Brief in Support of Its Motion to Stay Pending Inter Partes Review, United States District Court for the District of Delaware, Demand for Jury Trial, Plaintiffs: *Intuitive Surgical, Inc. and Intuitive Surgical Operations, Inc.*, V. Defendant: *Auris Health, Inc*, Case No. 18-1359-MN, Document 126, Nov. 15, 2019, 13 pages.

Defendant Auris Health, Inc.'s Reply Brief in Support of Its Motion to Transfer Venue Pursuant to 28 U.S.C. § 1404(a), United States District Court for the District of Delaware, Plaintiffs: *Intuitive Surgical, Inc. and Intuitive Surgical Operations, Inc.*, V. Defendant: *Auris Health, Inc*, C.A. No. 18-1359-MN, Document 31, Nov. 18, 2018, 14 pages.

Demand for Jury Trial Public Redacted Version, Declaration of Jamie L. Kringstein in Support of Defendant Auris Health, Inc.'s Renewed Motion to Stay Pending Inter Partes Review, C.A. No. 18-1359-MN, Document 215, Mar. 12, 2020, 5 pages.

Desai M.M., et al., "Flexible Robotic Retrograde Renoscopy: Description of Novel Robotic device and Preliminary Laboratory Experience," Urology, Jul. 2008, vol. 72 (1), pp. 42-46.

DiMaio S., et al., "The da Vinci Surgical system," Surgical Robotics : System Applications and Visions, Chap. 9, 2011, pp. 199-217.

Exhibit 1, Plaintiffs Intuitive Surgical, Inc. And Intuitive Surgical Operations, Inc.'s Preliminary Election of Asserted Claims, United States District Court for the District of Delaware, Plaintiffs: *Intuitive Surgical, Inc. and Intuitive Surgical Operations, Inc.*, V. Defendant: *Auris Health, Inc*, Case No. 1:18-cv-01359-MN, Demand for Jury Trial, Document 119-1, Aug. 9, 2019, 5 pages.

Exhibit 1, Before Ulrike W. Jenks, Tina E. Hulse, and James A. Worth, Administrative Patent Judges, Petitioner: *Auris Health, Inc* v. Patent Owner. *Intuitive Surgical Operations, Inc.*, IPR2019-01173, Document 215-1, Entered: Dec. 16, 2019, 197 pages.

Exhibit 1, Declaration, Annual Report Pursuant to Section 13 or 15(D) of the Securities Exchange Act of 1934, United States Securities and Exchange Commission, Form 10-K, Case 1:18-cv-01359-MN, Intuitive Surgical, Inc, Document 28-1, 2018, 12 pages.

Exhibit 1, Fox Chase Cancer Center Among First in U.S. To Use Innovative Technology for Lung Cancer Diagnosis, Temple Health, Retrieved from the Internet: (https://www.foxchase.org/news/2018-08-15-Monarch-Robotic-Bronchoscopy), Case 1:18-cv-01359-MN, Document 23-3, Aug. 15, 2018, 4 pages.

Exhibit 1, Morrison & Foerster, via Email, *Intuitive Surgical, Inc.* v. *Auris Health, Inc*, Case No. 1:18-cv-01359-MN, Sep. 9, 2019, Document 127-1, 22 pages.

Exhibit 1, Subpoena to Produce Documents, Information, or Objects or to Permit Inspection of Premises in a Civil Action, Stryker Corporation, Plaintiffs: *Intuitive Surgical, Inc. et al.*, V. Defendant: *Auris Health, Inc*, Civil Action No. 18-1359-MN, Document 158-1, held on Jan. 27, 2020, 42 pages.

Exhibit 1, Subpoena to Testify at a Deposition in a Civil Action, Amir Belson, Plaintiffs: *Intuitive Surgical, Inc. et al.*, V. Defendant: *Auris Health, Inc*, Civil Action No. 18-1359-MN, Document 188-1, held on Mar. 12, 2020, 9 pages.

Exhibit 1, Subpoena to Testify at a Deposition in a Civil Action, Gunter D. Niemeyer, Plaintiffs: *Intuitive Surgical, Inc. et al.*, V. Defendant: *Auris Health, Inc*, Civil Action No. 18-1359-MN, Document 148-1, held on Jan. 29, 2020, 9 pages.

Exhibit 1, Subpoena to Testify at a Deposition in a Civil Action, Hari Das Nayar, Plaintiffs: *Intuitive Surgical, Inc. et al.*, V. Defendant: *Auris Health, Inc*, Civil Action No. 18-1359-MN, Document 154-1, held on Jan. 29, 2020, 44 pages.

Exhibit 1, Subpoena to Testify at a Deposition in a Civil Action, Joseph M. Tartaglia, Plaintiffs: *Intuitive Surgical, Inc. et al.*, V. Defendant: *Auris Health, Inc*, Civil Action No. 18-1359-MN, Document 149-1, held on Jan. 30, 2020, 9 pages.

Exhibit 1, Subpoena to Testify at a Deposition in a Civil Action, Paul Schenker, Plaintiffs: *Intuitive Surgical, Inc. et al.*, V. Defendant: *Auris Health, Inc*, Civil Action No. 18-1359-MN, Document 155-1, held on Jan. 30, 2020, 44 pages.

Exhibit 1, Subpoena to Testify at a Deposition in a Civil Action, Robert H. Sturges, Jr., Plaintiffs: *Intuitive Surgical, Inc. et al.*, V. Defendant: *Auris Health, Inc*. Civil Action No. 18-1359-MN, Document 156-1, held on Jan. 28, 2020, 44 pages.

Exhibit 1, Subpoena to Testify at a Deposition in a Civil Action, Steve Charles, Plaintiffs: *Intuitive Surgical, Inc. et al.*, V. Defendant: *Auris Health, Inc*, Civil Action No. 18-1359-MN, Document 157-1, held on Jan. 27, 2020, 44 pages.

Exhibit 1, United States District Court for the District of Delaware, Subpoena to Testify at a Deposition in a Civil Action, to Carolyn M. French, C/O Dude Tangri LLP, Case 1:18-cv-01359-MN, Document 150-1, Dec. 23, 2019, 9 pages.

Exhibit 1, United States District Court for the District of Massachusetts, Subpoena to Testify at a Deposition in a Civil Action, to Philips Electronics North America Corporation, Case 1:18-cv-01359-MN, Document 104-1, Oct. 17, 2019, 28 pages.

Exhibit 1, United States District Court for the District of Minnesota, Subpoena to Testify at a Deposition in a Civil Action, to Covidien Holding Inc., Case 1:18-cv-01359-MN, Document 96-1, Oct. 8, 2019, 9 pages.

Exhibit 10, From: Dawson, Shaelyn K, Subject: *Intuitive* v. *Auris*: Summary of Sep. 26, 2019 meet-and-confer re: Intuitive's deficient production, Case 1:18-cv-01359-MN, Document 119-10, 2019, 4 pages.

Exhibit 11, U.S Food and Drug Administration, Case 1:18-cv-01359-MN, Document 119-11, Auris Surgical Robotics, Inc, Mar. 22, 2018, 12 pages.

Exhibit 12, United States Securities and Exchange Commission, Form D, Notice of Exempt Offering of Securities, Case 1:18-cv-01359-MN, Document 28-12, 2018, 7 pages.

Exhibit 2, Declaration, "Pairing Human Ingenuity with Technology, " Intuitive, Case 1:18-cv-01359-MN, Document 28-2, 2018, 13 pages.

Exhibit 2, Petition for Inter Partes Review of U.S. Pat. No. 8,801,601, USPTO, Petitioner: Auris Health, Inc, Patent Owner Intuitive Sur-

(56) References Cited

OTHER PUBLICATIONS gical Operations, Inc, Case 1:18-cv-01359- MN, Document 119-2, Inter Partes Review No. IPR2019-01173, Jun. 12, 2019, 85 pages.

Exhibit 2, UPMC Hamot First in U.S. To Use Innovative Robotic Technology to Detect Lung Cancer Earlier, Upmc Life Changing Medicine, Case No. 1:18-cv-01359-MN, Document 23-4, 2018, 3 pages.

Exhibit 3, Declaration, Contact Intuitive, Office locations and contact Information, Case 1:18- cv-01359-MN, Document 28-3, 2018, 5 pages.

Exhibit 3, Petition for Inter Partes Review of U.S. Pat. No. 6,800,056, USPTO, Petitioner: Auris Health, Inc, Patent Owner Intuitive Surgical Operations, Inc, Case 1:18-cv-01359-MN, Document 119-3, Inter Partes Review No. IPR2019-01189, Jun. 13, 2019, 73 pages.

Exhibit 4, "da Vinci Robotic Surgery, " Christiana Care Health System, Helen F. Graham Cancer Center & Research Institute, Case 1:18-cv-01359-MN, Document 28-4, 2018, 3 pages.

Exhibit 4, Letter, Robotic Bronchoscopy for Peripheral Pulmonary Lesions, ClinicalTrials.gov, Document 23-6, Retrieved from the Internet: (https://clinicaltrials.gov/ct2/show/NCT03727425), Auris Health, Inc, Case 1:18-cv-01359-Mn, Document 23-6, ClinicalTrials.gov Identifier: NCT03727425, 2018, 9 pages.

Exhibit 4, Petition for Inter Partes Review of U.S. Pat. No. 6,246,200, USPTO, Before the Patent Trial and Appeal Board, Petitioner: Auris Health, Inc, Patent Owner Intuitive Surgical Operations, Inc, Case 1:18-cv-01359-Mn, Inter Partes Review No. IPR2019-01448, Document 119-4, Aug. 5, 2019, 86 pages.

Exhibit 5, "Auris Health, Ethicon's Neuwave Ink Robot-assisted Bronchoscope Ablation Dev Deal," May 16, 2018, by Fink Densford, Retrieved from the Internet: (https://https://www.massdevice.com/auris-health-ethicons-neuwave-ink-robot-assisted-bronchoscope-ablation-dev-deal/), Case 1:18-cv-01359-MN, Document 23-7, 2018, Massdevice Medical Network, 12 pages.

Exhibit 5, Declaration, "Beebe Healthcare Introduces the da Vinci® Xi™ Robotic Surgical System," Submitted by Rachel on Jun. 8, 2018, Case 1:18-cv-01359-MN, Document 28-5, 4 pages.

Exhibit 5, Petition for Inter Partes Review of U.S. Pat. No. 9,452,276, USPTO, Before the Patent Trial and Appeal Board, Petitioner: Auris Health, Inc, Patent Owner Intuitive Surgical Operations, Inc, Case 1:18-cv-01359-MN, Inter Partes Review No. IPR2019-01496, Document 119-5, Aug. 15, 2019, 72 pages.

Exhibit 6, Declaration, "Fox Chase Cancer Center Among First in U.S. To Use Innovative Technology for Lung Cancer Diagnosis," Philadelphia International Medicine® News Bureau, Fox Chase Cancer Center Temple Health, for Immediate Release, Case 1:18-cv-01359-MN, Document 28-6, Aug. 23, 2018, 3 pages.

Exhibit 6, Petition for Inter Pates Review of U.S. Pat. No. 8,142,447, Before the Patent Trial and Appeal Board, Petitioner: Auris Health, Inc, Patent Owner Intuitive Surgical Operations, Inc, Case 1:18-cv-01359-MN, Inter Pates Review No. IPR2019-01533, Document 119-6, Aug. 29, 2019, 84 pages.

Exhibit 7, Petition for Inter Partes Review of U.S. Pat. No. 6,491,701, Before the Patent Trial and Appeal Board, Petitioner: Auris Health, Inc, Patent Owner Intuitive Surgical Operations, Inc, Case 1:18-cv-01359-MN, Inter Partes Review No. IPR2019-01532, Document 119-7, Aug. 29, 2019, 79 pages.

Exhibit 7, "Upmc Hamot First in U.S. To Use Innovative Robotic Technology to Detect Lung Cancer Earlier, " UPMC Life Changing Medicine, Case No. 1:18-cv-01359-MN, Document 28-7, 2018, 3 pages.

Exhibit 8, Careers Audacious goals. Audacious challenges, Auris, Retrieved from the Internet: (URL:http://https://www.aurishealth.com/jobs?gh_jid=1256912), Case 1:18-cv-01359-MN, Document 28-8, 2018, 8 pages.

Exhibit 8, Petition for Inter Partes Review of U.S. Pat. No. 6,522,906, USPTO, Before the Patent Trial and Appeal Board, Petitioner: Auris Health, Inc, Patent Owner Intuitive Surgical Operations, Inc, Case 1:18-cv-01359-MN, IPR2019-01547, Document 119-8, Aug. 30, 2019, 82 pages.

Exhibit 9, "Robotic Bronchoscopy for Peripheral Pulmonary Lesions, " ClinicalTrials.gov, U.S. National Library of Medicine, ClinicalTrials.gov Identifier: NCT03727425, Auris Health, Inc, Case 1:18-cv-01359-MN, Document 28-9, 2018, 8 pages.

Exhibit 9, Trial Statistics, USPTO, Case 1:18-cv-01359-MN, Document 119-9, 2019, 12 pages.

Exhibit A, Letter, *Intuitive Surgical, Inc. and Intuitive Surgical Operations, Inc. v. Auris Health, Inc.*, Case 1:18-cv-01359-MN, Doc 53-1, 2019, 86 pages.

Exhibit B, Plaintiffs Intuitive Surgical, Inc. and Intuitive Surgical Operations, Inc.'s First Set of Requests for Production of Documents to Defendant Auris Health, Inc, United States District Court for the District of Delaware, Plaintiffs: *Intuitive Surgical, Inc. and Intuitive Surgical Operations, Inc.*, V. Defendant: *Auris Health, Inc*, Case No. 1:18-cv-01359-LPS, Document 23-2, Dec. 3, 2018, 9 pages.

Extended European Search Report for Application No. EP19195298.5 dated Nov. 12, 2019, 10 pages (ISRG04151D1/EP).

Joint Appendix to Claim Construction Brief, United States District Court for the District of Delaware, Plaintiffs: *Intuitive Surgical, Inc. and Intuitive Surgical Operations, Inc.*, V. Defendant: *Auris Health, Inc*, Case No. 1:18-cv-01359-MN, Document 114, Oct. 29, 2019, 4 pages.

Joint Claim Construction Brief, United States District Court for the District of Delaware, Plaintiffs: *Intuitive Surgical, Inc. and Intuitive Surgical Operations, Inc.*, V. Defendant: *Auris Health, Inc*, Case No. 1:18-cv-01359-MN, Document 113, Oct. 29, 2019, 103 pages.

Joint Claim Construction Chart, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Document 76, Aug. 2, 2019, 31 pages.

Koolwal a.B., "An Image-based Localization Algorithm for Catheter Navigation in the Left Atrium," Experimental Robotics: the Eleventh International Symposium, 2009, pp. 251-260.

Le Roux, P.D., et al., "Robot-assisted Microsurgery: A Feasibility Study in the Rat," Neurosurgery, Mar. 2001, vol. 48 (3), pp. 584-589.

Markman Hearing, Before: The Honorable Maryellen Noreika, Case No. 18-1359(MN), Plaintiffs: Intuitive Surgical, Inc., Defendant: Auris Health, Inc., held on Nov. 20, 2019, pp. 1-162.

Markman Hearing, Before: the Honorable Maryellen Noreika, Case No. 18-1359(MN), Plaintiffs: Intuitive Surgical, Inc., Defendant: Auris Health, Inc., held on Nov. 20, 2019, pp. 1-139.

Memorandum Opinion, United States District Court for the District of Delaware, Plaintiffs: *Intuitive Surgical, Inc. and Intuitive Surgical Operations, Inc.*, V. Defendant: *Auris Health, Inc*, Case No. 18-1359 (MN), May 31, 2019, 13 pages.

Memorandum Order, United States District Court for the District of Delaware, Plaintiffs: *Intuitive Surgical, Inc. and Intuitive Surgical Operations, Inc.*, V. Defendant: *Auris Health, Inc*, Case No. 18-1359 (MN), 2019, 16 pages.

Mendivil A., et al., "Emergence of Robotic Assisted Surgery in Gynecologic Oncology American Perspective," Gynecologic Oncology, Aug. 2009, vol. 114, pp. S24-S31.

Motion to Stay, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Document 117, Oct. 30, 2019, 2 pages.

Office Action for U.S. Appl. No. 15/134836, dated Feb. 25, 2019, 4 pages.

Office Action dated Nov. 21, 2019 for Korean Application No. 10-2019-7025657 filed on 10 May 2012, 19 pages. (ISRG02620D1/KR).

Patent Owner's Mandatory Notices of U.S. Pat. No. 8,142,447, Before the Patent Trial and Appeal Board, Petitioner: Auris Health, Inc, Patent Owner: Intuitive Surgical Operations, Inc, IPR2019-01533, Sep. 12, 2019, 7 pages.

Patent Owner's Preliminary Response for U.S. Pat. No. 6,491,701, Review No. IPR2019-01532 dated Dec. 10, 2019, 20 pages.

Patent Owner's Preliminary Response for U.S. Pat. No. 8,142,447, Review No. IPR2019-01533 dated Dec. 10, 2019, 27 pages.

Petitioner's Updated Exhibit List of U.S. Pat. No. 6,491,701, review No. IPR2019-01532 dated Dec. 5, 2019, pp. 1-4.

(56) References Cited

OTHER PUBLICATIONS

Petitioner's Updated Exhibit List of U.S. Pat. No. 6,491,701, review No. IPR2019-01532 dated Dec. 9, 2019, pages.
Petitioner's Updated Exhibit List of U.S. Pat. No. 8,142,447, review No. IPR2019-01533 dated Dec. 5, 2019, pp. 1-4.
Petitioner's Updated Exhibit List of U.S. Pat. No. 8,142,447, review No. IPR2019-01533 dated Dec. 9, 2019, pp. 1-4.
Plaintiffs Intuitive Surgical, Inc. And Intuitive Surgical Operations, Inc.'s Opposition to Defendant Auris Health, Inc.'s Motion to Transfer, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Document 26, Dec. 11, 2018, 23 pages.
Plaintiffs' Opposition to Defendant's Motion to Stay, United States District Court for the District of Delaware, Plaintiffs: *Intuitive Surgical, Inc. and Intuitive Surgical Operations, Inc.*, V. Defendant: *Auris Health, Inc*, Case No. 18-1359-MN, Document 121, Nov. 13, 2019, 21 pages.
Prosecution History for U.S. Pat. No. 8142447 dated Jan. 30, 2019, 1871 pages.
PTAB Teleconference for review No. IPR2019-01496 dated Dec. 6, 2019, Petitioner Auris Health, Inc, pp. 1-33.
Report on the Filing or Determination of an Action Regarding a Patent or Trademark, To: Mail Stop 8, Director of USPTO, Alexandria, VA, Case 1:18-cv-01359-MN, Document 3, 2018, 2 pages.
Sackier J.M., et al., "Robotically Assisted Laparoscopic Surgery, From Concept to Development," Surgical Endoscopy, Springer-Verlag, 1994, vol. 8 (8), pp. 63-66.
Saraf S., "Robotic Assisted Microsurgery (RAMS): Application in Plastic Surgery", Medical robotics, Ch.3, 2008, pp. 363-376.
Schenker P.S., et al., "A New Robotic for High Dexterity Microsurgery," Conference of Computer Vision, Virtual Reality and Robotics in Medicine, 1995, pp. 116-122.
Shaw Keller Llp, Letter, the Honorable Maryellen Noreika, Case 1:18-cv-01359-MN, *Intuitive Surgical, Inc., et al.* v. *Auris Health, Inc.*, Document 123, by CM/ECF & Hand Delivery, Nov. 13, 2019, 1 page.
Solomon S.B., et al., "Three-dimensional CT-guided Bronchoscopy with a Real-time Electromagnetic Position Sensor a Comparison of two image registration methods," Chest, Dec. 2000, vol. 118 (6), pp. 1783-1787.
Stipulation Regarding Prior art, United States District Court for the District of Delaware, Plaintiffs: *Intuitive Surgical, Inc. and Intuitive Surgical Operations, Inc.*, V. Defendant: *Auris Health, Inc*, Demand for Jury Trial, CA No. 18-1359-MN, Mar. 4, 2020, 4 pages.
Stipulation Regarding U.S. Pat. No. 8,142,447, Plaintiffs: *Intuitive Surgical, Inc. and Intuitive Surgical Operations, Inc.*, V. Defendant: *Auris Health, Inc*, C.A. No. 18-1359-MN, Mar. 20, 2020, 2 pages.
Sturges R.H. Jr., et al., "A Voice-Actuated, Tendon-Controlled Device for Endoscopy", 1996, pp. 603-617.
Sturges, Robert H. et al., "A Flexible, Tendon-Controlled Device for Endoscopy," The International Journal of Robotics Research, 1993, vol. 12(2), pp. 121-131.
Tarn T.J., et al., "Coordinated control of Two Robot Arms," Proceedings of IEEE International Conference on Robotics and Automation, 1986, pp. 1193-1202.
Taylor, Russell H. et al., "A Telerobotic Assistant for Laparoscopic Surgery," IEEE Engineering in Medicine and Biology, May/Jun., 1995, pp. 279-288, vol. 14, Issue 3, IEEE.
Transcript Teleconference, United States District Court for the District of Delaware, Plaintiffs: *Intuitive Surgical, Inc. and Intuitive Surgical Operations, Inc.*, V. Defendant: *Auris Health, Inc*, Case No. 18-1359(MN), Document 58, 2019, 11 pages.
Transcript, United States District Court for the District of Delaware, Plaintiffs: *Intuitive Surgical, Inc. and Intuitive Surgical Operations, Inc.*, V. Defendant: *Auris Health, Inc*, Case No. 18-1359-(MN), Document 83, 9 pages.
Uchiyama, M., et al., "Hybrid Position/Force Control for Coordination of a Two-art Robot," Proceedings of IEEE International Conference on Robotics and Automation, 1987, pp. 1242-1247.
Weller S., He Helped Pioneer Robotic Surgery. Now He Wants to Reinvent Lung Cancer Care, JNJ.com, Case 1:18-cv-01359-MN, Document 114-2, Apr. 2019, 155 pages.
Zhou H.X., et al.,"Clinical Characteristics of Remote Zeus Robot Assisted Laparascopic Cholecystectomy: A Report of 40 Cases," World Journal of Gastroenterology, Apr. 2006, vol. 12 (16), pp. 2606-2609.

* cited by examiner

PASSIVE PRELOAD AND CAPSTAN DRIVE FOR SURGICAL INSTRUMENTS

CROSS-REFERENCE TO RELATED APPLICATIONS

This application is a continuation application of U.S. application Ser. No. 15/001,948, filed Jan. 20, 2016, which is a continuation application of U.S. application Ser. No. 12/286,644, filed Sep. 30, 2008, and issued as U.S. Pat. No. 9,259,274, filed Sep. 30, 2008 on Feb. 16, 2016, both of which are incorporated herein by reference in its entirety their entireties.

BACKGROUND

Robotically (as used herein, the terms "robot" or "robotically" and the like include teleoperation or telerobotic aspects) controlled instruments are well known and often used in minimally invasive medical procedures. FIG. 1 shows an example of an instrument 100 having a structure that is simplified to illustrate basic working principles of some current robotically controlled medical instruments. Instrument 100 includes a tool or end effector 110 at the distal end of a shaft 120. The proximal end of shaft 120 attaches to a transmission or drive mechanism 130 that is sometimes referred to as backend mechanism 130. During a medical procedure, end effector 110 and the distal end of shaft 120 can be inserted through a small incision or a natural orifice of a patient to position end effector 110 at a work site in the patient. End effector 110 as illustrated includes jaws 112 and 114 that may be used at the work site for clamping, gripping, cutting, or other purposes. Other types of end effectors, for example, scalpels, wire loops, and cauterizing instruments, are known and could alternatively be mounted on the distal end of shaft 120. Normally, a surgical instrument would further include a wrist mechanism (not shown) at the distal end of shaft 120 to provide additional degrees of freedom of motion for positioning, orienting, and using end effector 110.

Tendons 121 and 122, which may be stranded cables, rods, tubes, or similar structures, run from backend mechanism 130 through shaft 120 and attach to end effector 110. A typical surgical instrument would also include additional tendons (not shown) that connect backend mechanism 130 to other structural members of end effector 110 or of a wrist mechanism, so that backend mechanism 130 can manipulate the tendons to operate end effector 110 and/or the wrist mechanism when performing the desired procedure at the work site. FIG. 1 illustrates two tendons 121 and 122 attached to jaw 112 in a pin joint structure, where jaw 112 is mounted for rotation about a pivot pin 116. To enable both clockwise and counterclockwise rotations of jaw 112, tendon 121 acts on jaw 112 at a moment arm about pivot pin 116 such that pulling on tendon 121 causes a torque tending to rotate jaw 112 clockwise in the view of FIG. 1. Similarly, tendon 122 acts at a moment arm such that pulling on tendon 122 causes a torque tending to rotate jaw 112 counterclockwise in the view of FIG. 1. Jaw 112 is thus provided with bi-directional actuation through pulling in a length of one tendon 121 or 122 and simultaneously releasing an identical length of the other tendon 122 or 121. Mechanisms other than pin joints are known or can be devised that provide bi-directional actuation of a distal joint through pulling in a length of one tendon 121 or 122 and releasing an equal and opposite length of the other tendon 122 or 121. For example, U.S. Pat. No. 6,817,974 (filed Jun. 28, 2002) entitled "Surgical Tool Having Positively Positionable Tendon-Actuated Multi-Disk. Wrist Support" by Cooper et al. and U.S. Pat. No. 6,394,998 (filed Sep. 17, 1999) entitled "Surgical Tools For Use In Minimally Invasive Telesurgical Applications" by Wallace et al., both of which are incorporated herein by reference, describe some known medical instrument structures in which actuation requires pulling one or more tendons while releasing lengths of one or more other tendons.

Slack in tendons 121 and 122 can cause malfunctions, for example, by permitting tendons 121 and 122 to derail from guides or pulleys (not shown) that route tendons 121 and 122 through instrument 100. Slack can also cause jumpy or unpredictable motion of the instrument. To avoid creating slack in tendon 121 or 122 when moving jaw 112, backend mechanism 130 operates to release a length of one tendon 121 or 122 while simultaneously reeling in an equal length of the other tendon 122 or 121. Tendons 121 and 122 can be attached to the same capstan 132 but wrapped in opposite directions to provide the desired movements of tendons 121 and 122 when a drive motor (not shown) turns capstan 132. In cases where an end effector has several degrees of freedom that are controlled by several tendons, for instance as described in U.S. Pat. Nos. 6,394,998 and 6,817,974, the backend mechanism can include mechanisms other than capstans to perform the function of releasing and reeling in related lengths of tendons in order to avoid slack in the tendons as distal joints are turned. It can be seen that tendons 121 and 122 can be two separate components, or they may be part of a closed loop component with a capstan actuator, such as that disclosed in U.S. Pat. No. 7,316,681 B2 (filed Oct. 4, 2005) entitled "Articulated Surgical Instrument For Performing Minimally Invasive Surgery With Enhanced Dexterity And Sensitivity" by Madhani et al., which is incorporated herein by reference.

Avoiding slack may also require tendons 121 and 122 to be pre-tensioned, particularly when end effector 110 may be used for pushing and pulling, clamping, gripping, or other actions that encounter resistance. In particular, backend mechanism 130 can apply tension to tendon 122 to cause jaw 112 to clamp down on material between jaws 112 and 114. Increasing tension in tendon 122 causes higher clamping force but also causes tendon 122 to stretch. To prevent the stretching of tendon 122 from causing a corresponding amount of slack in tendon 121, tendon 121 can be preloaded with a tension that stretches tendon 121. For example, assuming tendons 121 and 122 are identical, tendon 121 can be pre-loaded with a tension about equal to or greater than maximum clamping tension used in tendon 122. As a result, tendon 121 starts stretched by the preloaded tension, and when applying a clamping force, the stretching of tendon 122 reduces the tension in tendon 121, allowing tendon 121 to contract without becoming slack.

The tensions preloaded in tendons can increase the forces that a backend mechanism must apply to operate an instrument. In particular, tension increases friction where tendons may ride on guides or solid surfaces. Also, if shaft 120 is a flexible tube such as might be employed to follow a natural lumen in a patient's body, the preloaded tension causes friction where tendons 121 and 122 contact curved surfaces of shaft 120. In all the above cases, increased friction quickly makes accurate control of the motion of end effector 110 difficult and can lead to, imprecise manipulation of, e.g., tissue, sutures, and needles during a surgical procedure. Further, preloading of the correct tension in tendons of a medical instrument can also increase the complexity of the manufacturing process of the medical instrument. Accordingly, medical instruments are desired that can avoid slack in drive tendons without requiring high preloaded tension.

SUMMARY

In accordance with an aspect of the invention, a passive preload system, such as a spring based mechanism, is attached to a tendon that is wrapped around a capstan, so that the passive preload system can control the relaxed tension in the tendon. The capstan can be driven by a motor when the tendon is needed to pull on a structural member of the instrument. For example, when applying clamping pressure or moving the structural member against resistance, capstan friction can produce tensions in the tendon that are many times the passive preload tension. However, when the tendon is not needed to apply force to the member, the capstan can be effectively and quickly made free to spin by zeroing or releasing the torque applied to the capstan by a drive motor, so that the passive preload system controls tendon tension and can provide just enough tension to prevent derailment or other malfunctions of the tendon. It should be noted that when the capstan is freed, the tendon can easily slide on the capstan since the tendon is not permanently attached to the capstan. In other words, forces are exchanged between the capstan and the tendon solely through friction. The reduced tension in relaxed tendons can reduce tendon friction, particularly in instruments with bent or flexible shafts. Two modes of operation of an instrument using a tendon attached to a passive preload system includes a mode where a motor turns a capstan about which the tendon is wrapped and thereby pulls on the tendon, and a mode where the capstan is freed and the tendon tension matches a tension of the passive preload system. A system can quickly switch between these two modes of operation by controlling the torque output by a drive motor and thus has a large bandwidth torque control.

One specific embodiment of the invention is a surgical instrument. The surgical instrument includes a shaft, a member mounted at a distal end of the shaft, a mechanism attached to a proximal end of the shaft, and a tendon. The member can be a link, or a jaw of an end effector, or a group of links coupled together, and the member is mounted to permit movement of the member relative to the shaft. The mechanism includes a capstan and a passive preload system, such as a spring system. The capstan can normally be free to roll and has a coupling through which a motor can attach to and rotate the capstan. The tendon has a first end attached to the member, runs down the shaft, wraps around the capstan, and has a second end attached to the passive preload system, which controls relaxed tension in the tendon.

Another specific embodiment of the invention is a robotic surgical system. The robotic surgical system includes a motor and an instrument coupled to the motor by means of a docking port. The robotic surgical system can also include an articulated arm holding the motor pack and the docking port. The instrument generally includes a shaft; a member mounted at a distal end of the shaft, a backend mechanism attached to a proximal end of the shaft, and a tendon. The member is mounted to permit movement of the member relative to the shaft. The backend mechanism includes a capstan and a passive preload system. The capstan is coupled to a drive motor in the docking port, so that the drive motor can rotate the capstan. The tendon has a first end attached to the member, runs down the shaft, wraps around the capstan, and has a second end attached to the passive preload system.

Yet another embodiment of the invention is a method for operating a surgical instrument containing a movable member, a first tendon attached for movement of the member in one direction, and a second tendon attached for movement of the member in another direction. The method includes: applying a torque to a first capstan about which a first tendon is wrapped; and at the same time, freeing from motor torques a second capstan about which the second tendon is wrapped so that a passive preload system attached to an end of the second tendon extending from the second capstan controls tension in the second tendon.

BRIEF DESCRIPTION OF THE DRAWINGS

Use of the same reference symbols in different figures indicates similar or identical items.

DETAILED DESCRIPTION

In accordance with an aspect of the invention, a surgical instrument can avoid tendon slack and maintain a relatively low tension in a relaxed drive tendon by wrapping the tendon around a capstan that is allowed to rotate freely and attaching an end of the tendon to a passive preload system such as a spring system. When operating the surgical instrument, friction between the tendon and the capstan allows a drive motor that turns the capstan to reel in a length of the tendon, and capstan friction can apply a maximum tension to the tendon that depends exponentially on the total angle of wrap the tendon about the capstan. The force from the passive preload system, e.g., spring force from a spring, and the tension in a relaxed tendon can therefore be kept relatively low while still being able to produce the high tensions needed for clamping or other movement of the instrument against resistance. When the motor torque on the capstan is zeroed, the capstan can rotate freely, and the passive preload system can pull in the tendon and prevent the tendon from becoming slack. The low relaxed tensions can decrease the forces needed for manipulation of the instrument, and tendon friction, which can be particularly problematic in medical instruments with curved or flexible shafts, can be reduced.

Figure 1:
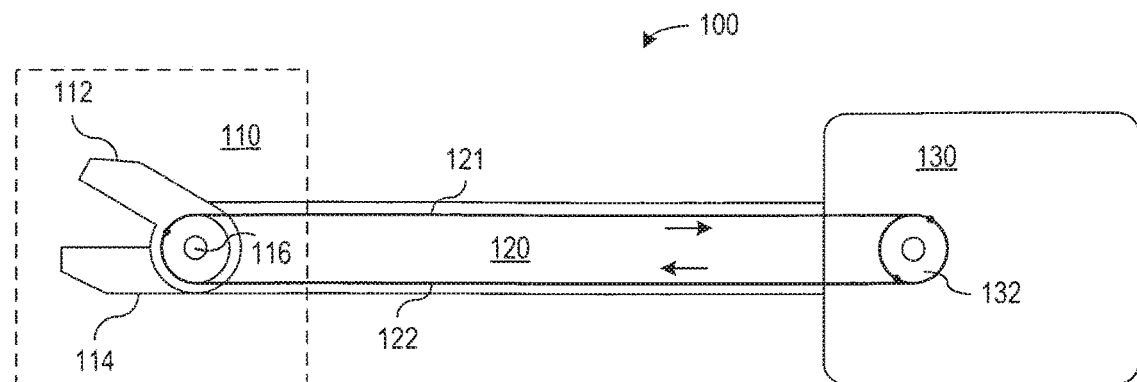
FIG. 1 shows a simplified version of a conventional robotically controlled medical instrument.
Figure 2A:
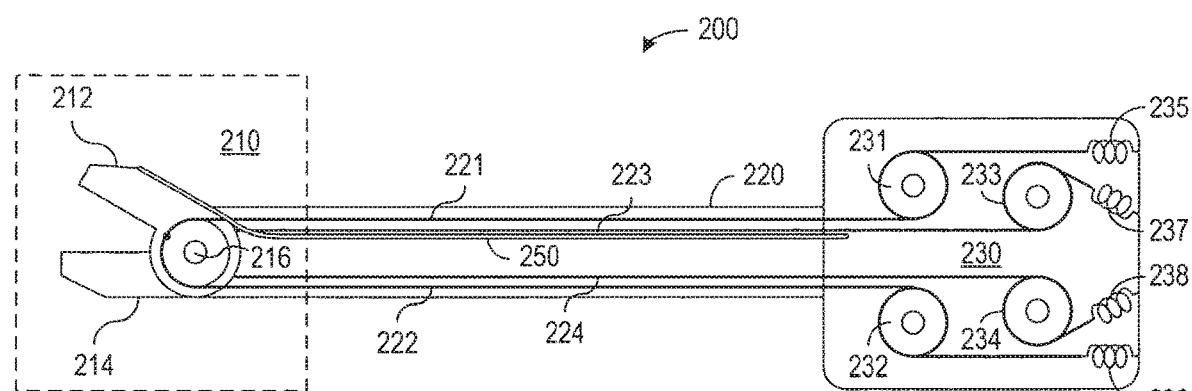
FIGS. 2A and 2B show a medical instrument in accordance with an embodiment of the invention using a spring and capstan friction to maintain a minimum tendon tension in the instrument.
Figure 2B:
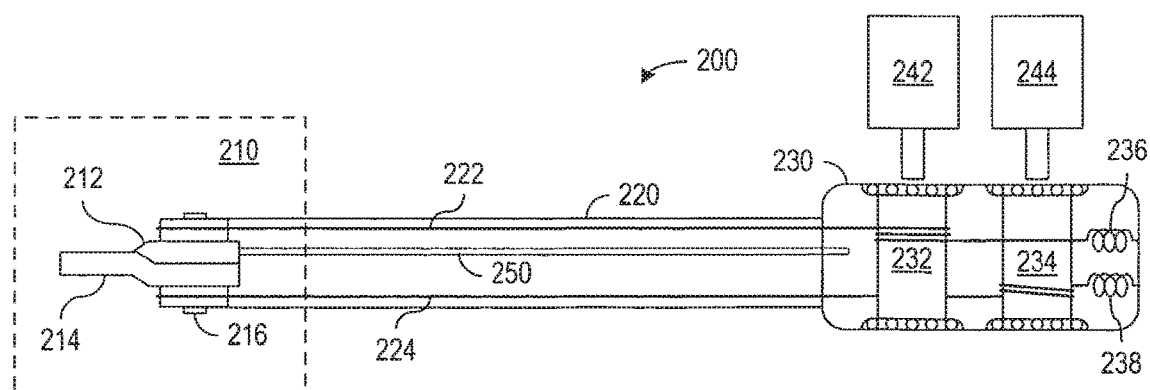

FIGS. 2A and 2B respectively show top and side views of a surgical instrument 200 in accordance with an embodiment of the invention. Instrument 200 includes an end effector 210 at a distal end of a shaft 220, which is connected to a backend mechanism 230. End effector 210 in the illustrated embodiment includes jaws 212 and 214, which are both mounted to enable relative movement of jaws 212 and 214. Jaws 212 and 214 can have shapes selected for the particular procedures for which effector 210 is intended. For example, jaws can be shaped to act as forceps of any desired type or could include blades that allow effector 210 to act as scissors. The materials and structure of jaws 212 and 214 can generally be selected for the particular uses of instrument 200, and many suitable effector architectures are known or may be developed.

Jaw 212 is connected to a first pair of tendons 221 and 222, and jaw 214 is connected to a second pair of tendons 223 and 224. Each pair of tendons 221 and 222 or 223 and 224 may be portions of a continuous tendon having a point that is attached to jaw 212 or 214, for example, by an adhesive or by a crimp residing in a notch in jaw 212 or 214. In a typical embodiment, additional tendons (not shown) would be connected in instrument 200 to a wrist mechanism or joints (not shown) that provide additional degrees of freedom for movement for positioning and orienting end effector 210.

Tendons 221, 222, 223, and 224 apply force and torques to jaws 212 and 214 when pulled by backend mechanism 230 and can have any structure suitable for that task. For example, tendons can be stranded cables, wires, rods, or tubes made of metal, a polymer, or other material. In an exemplary embodiment, tendons 221, 222, 223, and 224 include portions of stranded cable that are fused to tubes, with the stranded cable being used where significant bending or flexing of the tendons is expected, and the tubes being used elsewhere to reduce stretching of the tendons. In another embodiment, particularly useful when shaft 220 is flexible, tendons 221, 222, 223, and 224 can be made of a woven polymer material and run inside individual sheaths (not shown).

FIGS. 2A and 2B illustrate the example embodiment where tendons 221, 222, 223, and 224 attach to a pivot joint structure in which relative motion of jaws 212 and 214 corresponds to independent rotations of jaws 212 and 214 about a pivot pin 216. This joint structure is only an example, and other mechanisms for moving members of a surgical instrument in response to tensions applied to tendons 221, 222, 223, and 224 are known and could be employed in alternative embodiments of the invention. For example, a planar, cylindrical, or spherical rolling joint could provide similar freedom of motion to jaws 212 and 214 in end effector 210, or a prismatic linear joint or slide could be employed in end effector 210 to provide a linear bidirectional degree of freedom of motion.

Shaft 220 is a hollow tube through which tendons 221, 222, 223, and 224 run. Shaft 220 may be rigid or flexible. For example, shaft 220 may be a rigid stainless steel tube if instrument 200 is intended to be inserted through a straight cannula during a medical procedure, but shaft 120 would need to be flexible if instrument 200 is intended to follow the variable path of natural lumens. In a typical configuration, shaft 220 may have a diameter of about 5 mm or 8 mm for use with some existing cannulae and may have a length on the order of several tens of centimeters. In case the shaft 220 is flexible, the tendons can run inside sheaths in a Bowden cable arrangement (i.e., like bicycle cables). As used herein, the term "flexible" includes continuously flexible components (such as a rubber tube, which bends at each point along its length) and constrained series of short, discrete links that allow the links to approximate the movement of a continuously flexible unit (such as a series "snake-like" vertebrae).

Backend mechanism 230 attaches to the proximal end of shaft 220 and acts as a transmission that converts the rotation of drive motors (e.g., drive motors 242 and 244 in FIG. 2B) into movement of end effector 210. Backend mechanism 230 particularly manipulates tendons 221, 222, 223, and 224 to operate end effector 210 and may additionally be able to rotate or move shaft 220 to change the orientation or position of end effector 210. In the illustrated embodiment, backend mechanism 230 includes one capstan 231, 232, 233, or 234 per tendon 221, 222, 223, or 224. In accordance with an aspect of the current invention, each tendon 221, 222, 223, or 224 wraps for a set wrapping angle (that could be less than a full turn or as large as one or more turns) around the corresponding capstan 231, 232, 233, or 234 and has an end extending from the capstan 231, 232, 233, or 234. Tendons 221, 222, 223, and 224 are not required to be permanently attached to capstans 231, 232, 233, and 234 and may be able to slip relative to the capstans 231, 232, 233, and 234.

The ends of tendons 221, 222, 223, and 224 attach to passive preload systems, here implemented as linear coiled springs 235, 236, 237, and 238, which can be anchored to a case or chassis of backend mechanism 230. Springs 235, 236, 237, and 238 are biased, e.g., stretched, so that springs 235, 236, 237, and 238 apply a non-zero force to respective attached tendons 221, 222, 223, and 224 throughout the range of motion of surgical instrument 200. With this configuration, when capstans 231, 232, 233, and 234 are free to rotate, the corresponding spring 235, 236, 237, or 238 controls the tension in the associated tendon 231, 232, 233, or 234 and avoids slack by pulling in the required length of tendon 231, 232, 233, or 234. Tendons 221, 222, 223, and 224 do not require a preloaded tension that is higher that the maximum tensions used for operation of surgical instrument 200.

Each passive preload system more generally can be any structure or system that is able to apply a force to the free end of a tendon while allowing the tendon end to displace. The preload system is passive in that the system does not need to respond to a control or feedback system. Such systems can use linear coil springs as illustrated in FIGS. 2A and 2B or use other spring elements, such as rotary coil springs, leaf springs or compliant members, such as bending beams, cantilever beams, or elastic bands. Further, the spring elements or compliant members can work through extension or compression to apply force directly or indirectly to the end of the attached tendons. Other methods for applying the desired force, such as a system using weights or magnets, might alternatively be employed. In addition to the source of force, the passive preload system may include mechanical elements that direct or control the magnitude of the force applied to the attached tendon.

End effector 210 can be operated using drive motors which are under the active control of human input (e.g., master control input in a master-slave servo control system) and software executed in a robotically controlled system. In particular, four drive motors, which are provided in a docking port of a control system (not shown), can be respectively coupled to capstans 231, 232, 233, and 234 of FIG. 2A. FIG. 2B shows two drive motors 242 and 244, which are coupled to capstans 232 and 234. The orientations of capstans 231, 232, 233, and 234 in backend mechanism 230 are not required to have particular fixed relations to the position or configuration of instrument 200. Accordingly, any mechanical coupling that allows a motor to rotate or apply a torque to a capstan can be used for the coupling of motors 242 and 244 to capstans 232 and 234 in backend mechanism 230.

Backend mechanism 230 can be removably attached to a motor pack including motors 242 and 244 through a sterile barrier, such as a sterile sheet of plastic, and the instrument 200 can be designed to be disposable or reusable and sterilizable. When the instrument is detached from the motor pack, the passive preload systems (e.g., springs 235, 236, 237, and 238 in FIG. 2A) still keep tendons 221, 222, 223, and 224 from slacking and allow end effector 210 and shaft 220 (when flexible) to be manually arranged (or posed) in any configuration without damaging backend mechanism 230 or creating slack in any tendons 221, 222, 223, or 224. This "backdriving" capability is generally a desirable property of a surgical instrument, particularly an instrument with a flexible shaft that may be bent or manipulated during instrument insertion while the instrument is not under active control. For example, the flexible shaft can be manually posed, and the tendons within the shaft do not experience undue tension or slack.

Figure 3A:
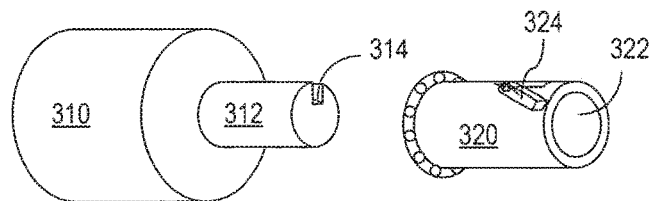
FIG. 3A shows a system in accordance with an embodiment of the invention that couples a drive motor to a capstan.

One system for mechanically coupling a motor to a capstan uses a friction connection where a pinion of the motor fits tightly into a bore in the capstan and relies on friction between the pinion and bore. Generally, when the motor rotates the capstan, the tendon wrapped around the capstan will tighten, which can increase the frictional connection when the capstan is sufficiently elastic to shrink in radius in response to the squeezing force from the tendons. FIG. 3A shows an alternative technique for mechanically coupling a drive motor 310 to a capstan 320. With this particular technique, a shaft 312 of drive motor 310 fits into a bore 322 of capstan 320. Shaft 312 has a slot 314, and capstan 320 has a spring loaded lever or other projection 324 that extends into bore 322. Projection 324 can be compressed when shaft 312 is inserted in bore 322, but projection 324 can spring back and engage slot 314 when slot 314 is rotated to become aligned with projection 324. Motor 310 can thus apply a torque to capstan 320. It should be understood that in other implementations, male-female mechanical relationships and their many variations can be reversed (e.g., so that a projection extends from the motor shaft and engages a slot in the capstan).

Figure 3B:
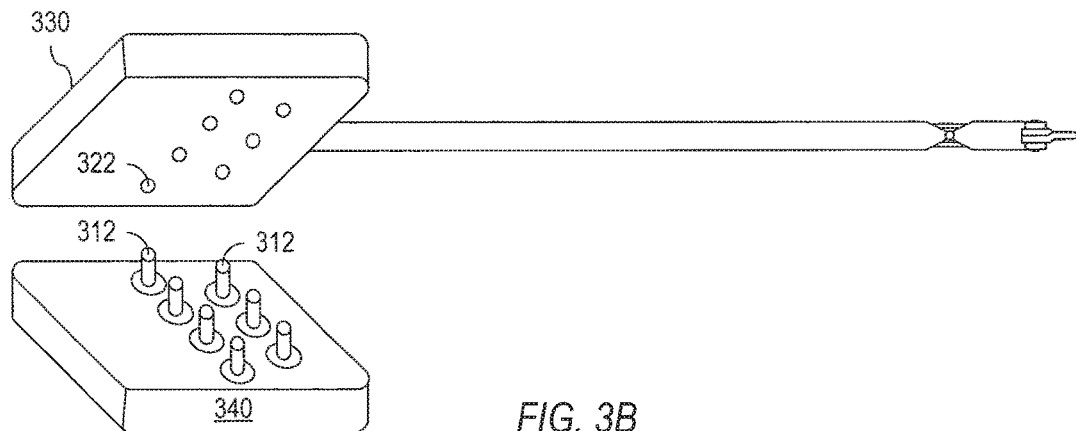
FIG. 3B shows a system in accordance with an embodiment of the invention in which capstans for multiple tendons engage a motor pack.

Backdriving capabilities of an instrument can also create situations where the orientation of capstan 320 relative to shaft 312 may be unknown when shaft 312 is inserted into bore 322. Regardless of the relative orientation, with the mechanical coupling of FIG. 3A, motor 312 can simply rotate shaft 312 until projection 324 engages slot 314. This ability is particularly important when a backend mechanism 330 includes multiple capstans arranged in an array to engage shafts 312 of motors in a motor pack 340 as illustrated in FIG. 3B, where all of the motor shafts 312 may have different and unknown orientations relative to the bores 322 of associated capstans.

The drive motors coupled to backend mechanism 230 of FIGS. 2A and 2B are generally operated to either apply a torque to the associated capstan or to allow the associated capstan to turn freely. In a process that controls a pair of tendons that are connected for rotation of a structural member of instrument 200, one drive motor applies a torque to a capstan around which one tendon is wrapped, and the capstan about which the other tendon is wrapped is allowed to freely rotate. For example, to rotate jaw 212 counterclockwise in the view of FIG. 2A, motor 242, which engages capstan 232, is activated and turns capstan 232 in a direction that pulls on tendon 222. The resulting torque that tendon 222 applies to jaw 212 tends to rotate jaw 212 counterclockwise toward jaw 214. The maximum tension that capstan 232 can apply to tendon 222 without tendon 222 slipping on capstan 232 is proportional to the force from spring 236 and increases exponentially with the wrap angle of tendon 222 about capstan 232. Accordingly, with a suitable wrap angle for tendon 222 about capstan 232, the force from spring 236 can be much less than the maximum tension that may need to be applied to tendon 222 when rotating jaw 212 against resistance. While capstan 232 pulls in tendon 222, capstan 231 is free to rotate and pays out a length of tendon 221 corresponding to the rotation of jaw 212. Capstan 221 being free to rotate allows the tension in the portion of tendon 212 between capstan 231 and jaw 212 to equalize with the tension in the portion of tendon 221 between capstan 231 and spring 235. Tendon 221 does not become slack, and the tension in tendon 221, which is controlled by spring 235, can be kept much lower than the maximum anticipated tension applied to tendon 222. When jaw 212 reaches the desired position and no clamping tension is required in tendon 222, both capstans 231 and 232 can be released to rotate freely. Clockwise rotation of jaw 212 can be achieved through operation of a drive motor coupled to capstan 231 to pull on tendon 221 while capstan 232 is left free to rotate. Rotations of jaw 214, or movements of other elements of instrument 200, can also be performed using similar procedures.

The control of jaws 212 and 214 and any joint in end effector 210 or shaft 220 can be effected in a closed loop by basing the motor control torques for that joint on measurement of the current position of the joint. Such measurements can, for example, be done by using a sensing technology such as the one described in U.S. Pat. App. Pub. No. US 2007/0156019 A1 (filed Jul. 20, 2006), entitled "Robotic Surgery System Including Position Sensors Using Fiber Bragg Gratings" by Larkin et al., and U.S. patent application Ser. No. 12/164,829 (filed Jun. 30, 2008) entitled "Fiber optic shape sensor" by Prisco, both of which are incorporated herein by reference. FIGS. 2A and 2B illustrate an illustrative shape sensing fiber 250 that extends to jaw 212 for sensing of the position of jaw 212. For the control loop, a control system compares a desired joint position with a measured joint position to compute a joint position error. A control or correction torque is then computed based on the current value of the joint position error, for instance using a Proportional Derivative Integral control law. Depending on the control torque sign indicating a clockwise or counterclockwise correction, one of the motors associated with the joint is commanded to apply a torque to its associated capstan while the other motor associated with the joint is commanded to zero its motor torque, thereby letting go of its associated capstan. In this way, the joint is placed in the desired position.

Figure 4:
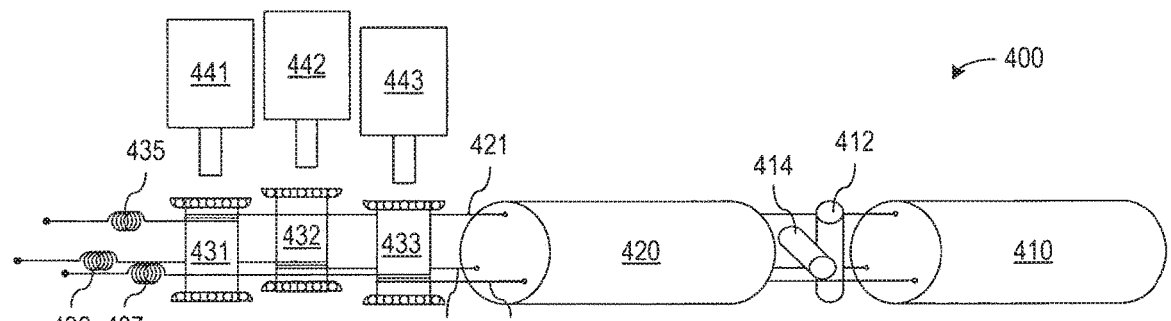
FIG. 4 is an expanded view schematically illustrating an embodiment of the invention using three capstans to control an instrument wrist or joint having two degrees of freedom corresponding to rotations about two perpendicular axes.

FIG. 4 illustrates portions of a medical instrument 400 in accordance with an embodiment of the invention using three tendons 421, 422, and 423 to control rotation of a structural member 410 about two perpendicular axes defined by pivots 412 and 414. Member 420 may be a link in a wrist or joint mechanism in an instrument shaft or in an end effector. Most of the mechanical structure associated with the joint and pivots 412 and 414 is omitted to better illustrate the operation of tendons 421, 422, and 423, but such joints can be implemented using known mechanical structures. Tendons 421, 422, and 423, which generally may be of the same type and construction as described above with reference to FIGS. 2A and 2B, attach to member 410 and extend back through a shaft 420 to a backend mechanism including capstans 431, 432, and 433 and passive preload systems 435, 436, and 437. Shaft 420 may generally be the same as shaft 220 described above. Also, in a manner similar to described above, each tendon 421, 422, or 423 wraps around a corresponding capstan 431, 432, or 433 and has an end attached to a corresponding passive preload system 435, 436, or 437. Passive preload systems 435, 436, and 437 can be anchored to the case or chassis of the backend mechanism.

Controlled rotation of member 410 about pivot 412 relies on tendons 421 and 422 being attached to member 410 at moment arms such that pulling tendon 421 or 422 can cause rotation of member 410 about pivot 412 in a direction that is opposite to the rotation that pulling on tendon 423 can cause. Similarly, rotation of member 410 about pivot 414 relies on tendons 422 and 423 being attached to member 410 at moment arms such that pulling tendon 422 or 423 can cause rotation of member 410 about pivot 414 in a direction that is opposite to the rotation that pulling on tendon 421 can cause. The desired relative anchoring of tendons 421, 422, and 423 can be achieved, for example, by terminating tendons 421, 422, and 423 on rays that extend at a 120° angles relative to each other from a central longitudinal axis of member 410. In operation of instrument 400, passive preload systems 435, 436, and 437 and drive motors 441, 442, and 443 create tensions in tendons 421, 422, and 423, and a control system (not shown) can control drive motors 441, 442, and 443 to balance the torques about pivots 412 and 414 as needed to achieve the desired relative orientation of member 410 or overcome resistance to the movement or stationary position of member 410. Sensors (not shown; see e.g., element 250 in FIGS. 2A and 2B) may be implanted in structural member 410 to provide feedback to the control system operating motors 441, 442, and 443. One illustrative example of a structural member 410 is a part of the parallel motion mechanism disclosed in U.S. Pat. App. Pub. No. US 2008/0065102 A1 (filed Jun. 13, 2007) entitled "Parallel Motion Mechanism" by Cooper, which is incorporated herein by reference.

The instruments described above employ passive preload systems to maintain a minimum relaxed tension in drive tendons. Passive preload systems as described above are readily implemented employing flexible members or springs, such as linear or rotational coil springs. Most common springs produce forces that are at least approximately described by Hooke's law over a range of forces and deflections. In particular, most springs apply a force that is proportional to the deflection of the spring from its equilibrium length. With Hooke's law springs, the tensions in relaxed tendons of an instrument of the types described above will depend on how far the springs are stretched, which in turn depends on the general configuration of the instrument, including the positions and orientations of the joints and effector in the instrument. This variation may not be significant if the range of motion of the tendons is small compared to the stretch already in the springs for biasing. However, simple Hooke's law springs will tend to create a minimal energy configuration for the instrument, and the instrument will tend to approach that configuration when all of the capstans are free to rotate. In practice, as mentioned above, this effect is small since the spring length change can be designed to be small compared to the spring bias. Further, spring systems that apply constant force can be used to avoid or reduce variations in the tensions in relaxed tendons.

Figure 5A:
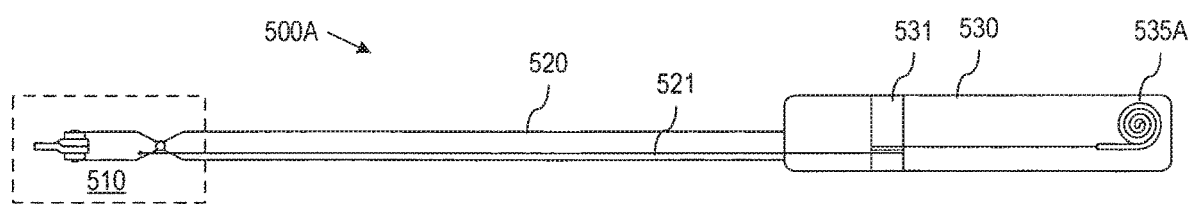
FIGS. 5A and 5B show embodiments of the invention employing constant-force spring systems to maintain constant tendon tension in relaxed tendons.

FIG. 5A shows a surgical instrument 500A in accordance with an embodiment of the invention employing a constant-force spring 535A. Instrument 500A includes an end effector 510, a shaft 520, and a backend mechanism 530, all of which can be substantially the same as described for similar elements above. A tendon 521 attaches to end effector 510, extends back through shaft 520 to backend mechanism 530, wraps around a capstan 531, and attaches to constant-force spring 535A. A constant-force spring is a spring that exerts a constant force over the range of motion of the spring. In the embodiment of FIG. 5A, constant-force spring 535A is a rolled ribbon of spring material that is relaxed when the ribbon is fully rolled up. As the ribbon unrolls, the portion of the ribbon near the roll produces the spring force. This spring force remains nearly constant as the ribbon unrolls because the portion of the ribbon that produces the spring force, i.e., the portion near the roll, has nearly the same shape as the spring unrolls.

Figure 5B:
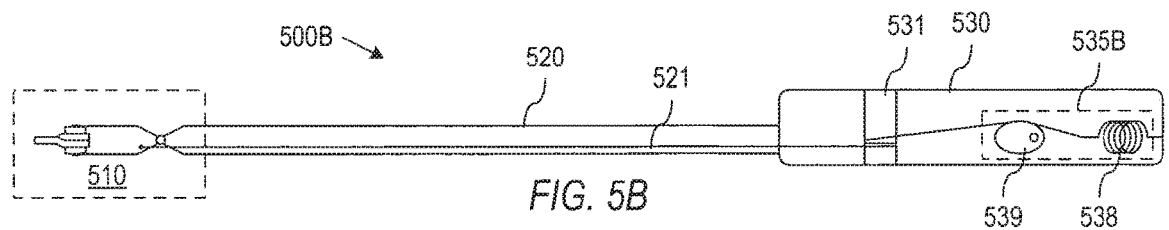

Constant-force spring systems can also be produced or approximated using a spring obeying Hooke's law and one or more cams or variable radius pulleys. FIG. 5B shows a surgical instrument 500B containing the same elements as in surgical instrument 500A, with the exception that constant-force sprig 535A is replaced with a constant-force spring system 535B that includes a spring element 538 that obeys Hooke's law and a variable radius cam 539. In particular, cam 539 has an input radius that is different from its output radius, with the ratio of the input radius and the output radius being the cam force transmission ratio at the specific angular position of cam 539. As spring element 538 extends, the input force to cam 539 increases proportionally and cam 539 rotates. The cam profile is designed to reduce the cam force transmission ratio as cam 539 rotates an amount that cancels the increase in input spring force. The spring element 538 can also be implemented, for example, as a linear spring, a rotational spring, or a leaf spring or as a compliant member such as a cantilever beam or elastic band. In one particular embodiment, spring element 538 is a rotational spring that is integrated with the cam 539 on the same cam axis. More details on constant spring forces are described in U.S. Pat. App. Pub. No. US 2004/0035243 A1 (filed May 22, 2003) entitled "Counter Balance System And Method With One Or More Mechanical Arms" by Duval, which is incorporated herein by reference.

Figure 6:
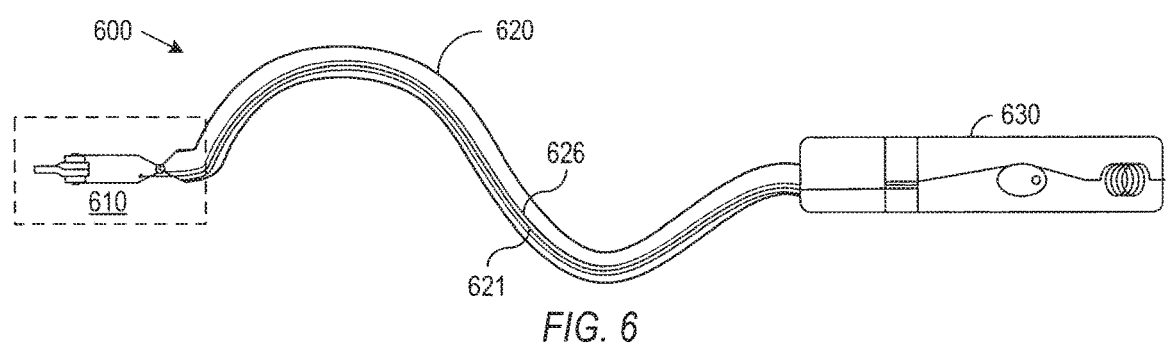
FIG. 6 shows a medical instrument in accordance with an embodiment of the invention having an effect or at the distal end of a flexible shaft.

The low tension maintained using techniques described above are particularly advantageous in surgical instruments having flexible shafts. FIG. 6, for example, illustrates a medical instrument 600 having an end effector 610 on the distal end of a shaft 620 that is flexible and bent into a curved, sinuous shape. Such bending may result during a minimally invasive medical procedure when end effector 610 and shaft 620 are guided through a natural lumen, such as a portion of the digestive tract of a patient. The shape of shaft 620 will generally be different during different procedures. A tendon 621 used to operate end effector 610 runs through flexible shaft 620 and therefore follows almost the same path as shaft 620, Tendon 621 may have a surrounding sheath 626 that is more rigid than tendon 621 to aid in guiding tendon 621 through shaft 620 and prevent lateral movement of tendon 621 during actuation of effector 610. Bends in shaft 620 can cause tendon 621 to ride on the solid surface of sheath 626, and frictional forces at these bends increase with the tension in tendon 621. Accordingly, reducing the relaxed tension in tendon 621 when shaft 620 is bent can reduce the force that backend mechanism 630 must be able to exert to operate effector 610. Backend mechanism 630 may thus be able to use small components that may not be robust enough to overcome the higher tendon friction that results from higher tendon tension.

Figure 7A:
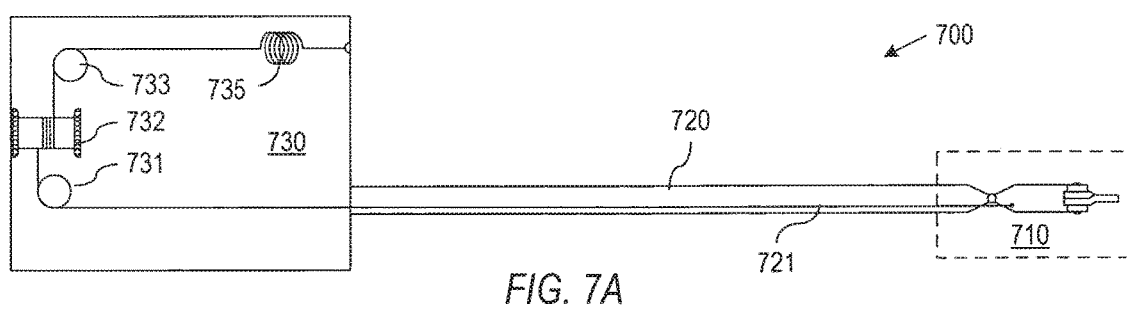
FIGS. 7A and 7B show side and perspective views of a medical instrument in accordance with an embodiment of the invention using drive motors with shafts parallel to the shaft of the instrument.

The above-described embodiments illustrate embodiments of surgical instruments having backend mechanisms in which capstans have rotation axes that are generally perpendicular to the direction of the instruments' shafts. However, many mechanical systems for routing and directing tendons are known and could be employed in a backend mechanism to alter configuration of the capstans. FIG. 7A, for example, illustrates an embodiment of a medical instrument 700 having a backend mechanism 730 containing a capstan 723 that has a rotation axis parallel to a shaft 720 on which an end effector 710 is mounted. In this embodiment, a tendon 721 attached to end effector 710 runs the length of shaft 730 into backend mechanism 730. Tendon 721 then winds around a first cam or pulley 731, wraps around capstan 732, winds around a second cam or pulley 733 and attaches to a spring 735 that is anchored in backend mechanism 730. Cams or pulleys 731 and 733 may be shaped to provide a constant tension in tendon 721 when tendon 721 is relaxed, even if spring 735 obeys Hooke's law.

Figure 7B:
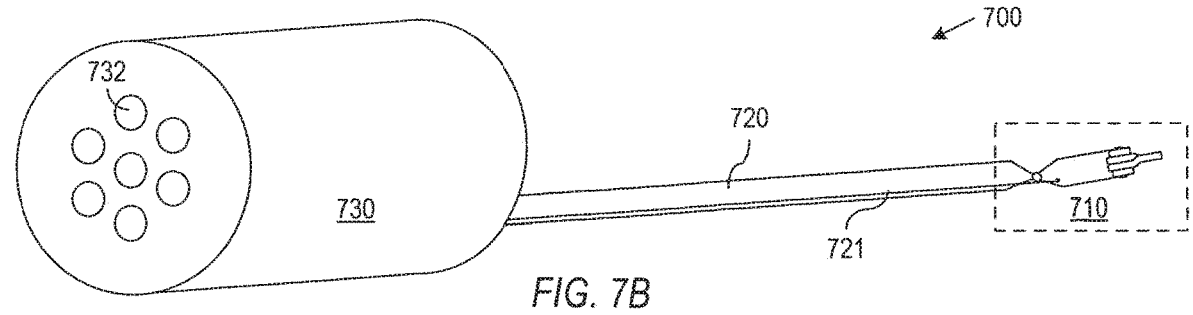

FIG. 7B shows that the bores of the capstans for multiple tendons in medical instrument 700 can be arranged on the back (most proximal surface) of backend mechanism 730. A docking port for instrument 700 can provide a matching array of motor shafts that fit into the bores of the capstans 732 for use of instrument 700 when instrument 700 is connected to the control system. As described above, many male-female mechanical mating configurations can be used, as well as many ways to rotationally align the capstans and motor shafts.

Figure 8:
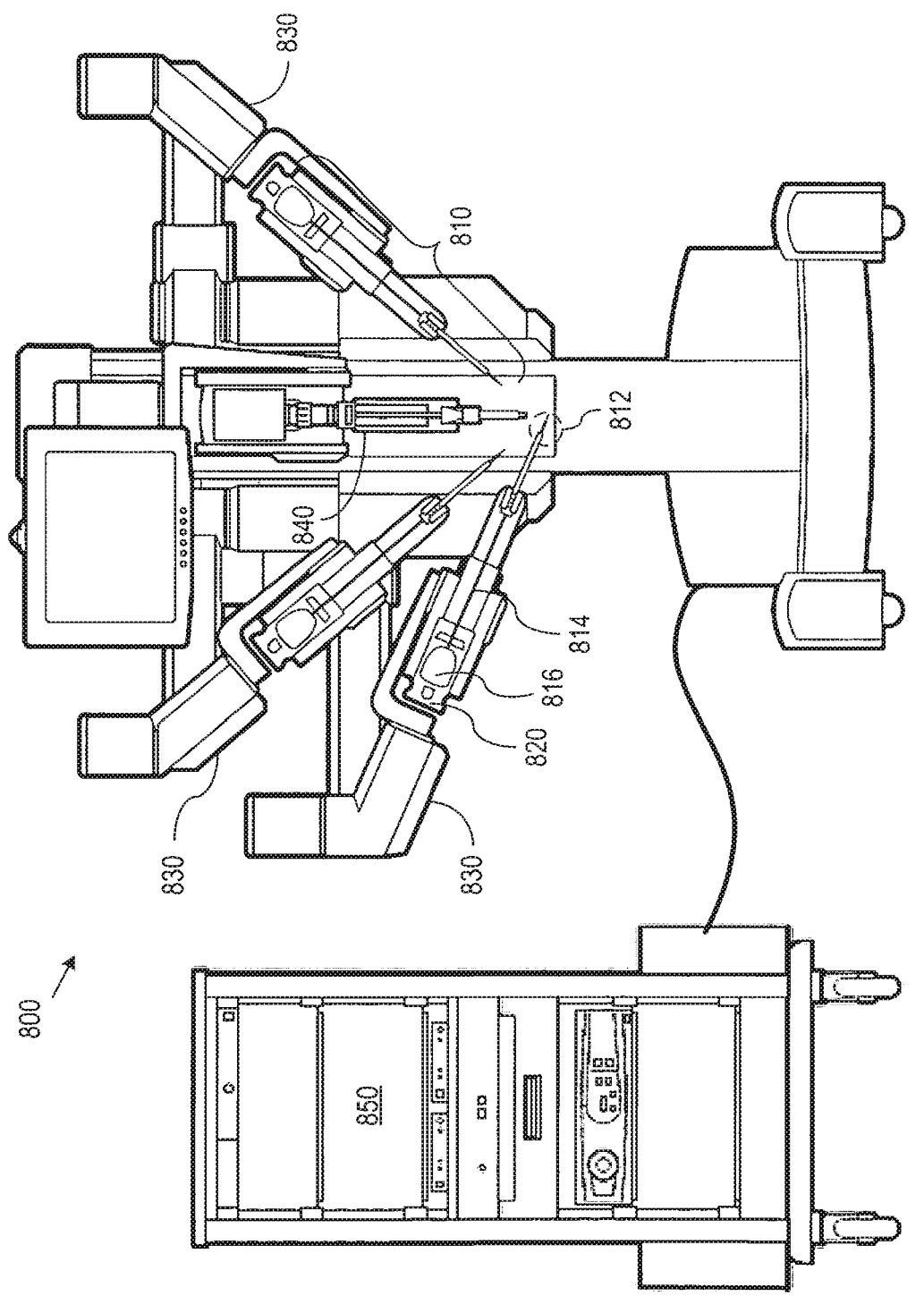
FIG. 8 shows a robotically controlled system in which medical instruments in accordance with embodiments of the present invention can be mounted for performance of medical procedures.

FIG. 8 shows an example of a robotically controlled system 800 capable of using medical instruments in accordance with embodiments of the present invention. System 800, which may, for example, be a da Vinci® Surgical System available from Intuitive Surgical, Inc. includes multiple surgical instruments 810, each of which is mounted in a docking port 820 on a robotic manipulator arm 830. Each instrument 810 generally includes an end effector 812, a shaft 814, and a backend mechanism 816, which may be of any of the types described above. In particular, instruments 810 may have shafts 816 that are rigid or flexible. When shafts 816 are flexible for insertion into and following of a natural lumen, robotically controlled and jointed arms 830 may not be needed, and instruments 810 can be mounted in mounting ports 820 on a cart or other fixed structure. Instruments 810 can be made interchangeable, so that the instruments 810 mounted in docking ports 820 can be selected for a particular medical procedure or changed during a medical procedure to provide the clinical functions needed. Instruments 810 can implement many functions, including but not limited to forceps or graspers, needle drivers, and scissors of many different shapes and sizes. An endoscopic camera, for example, a stereoscopic camera, can also be mounted on an arm 840 to provide visual information, particularly images, of the work site at which instruments 810 are operating.

Docking ports 820 generally include drive motors that provide mechanical power for operation of instruments 810 and systems for establishment of a sterile barrier between instrument 810 and the rest of robotically control system 800. Some suitable sterile barriers are described in U.S. Pat. No. 6,132,368 (filed Nov. 21, 1997) entitled "Multi-Component Telepresence System And Method" by Cooper, which is incorporated herein by reference. Docking ports 820 may additionally include an electrical interface for communication with instruments 810, for example, to identify the type of instrument in the docking port and to access parameters of the instrument. The electrical interface may also convey measurements such as measurements of the position and orientation of effectors 812 or shaft 814. A computer system 850 can receive the measurements and execute software that controls drive motors in the docking ports 820 as needed to manipulate instruments 810 as directed by a surgeon or other medical personnel using system 800 to perform a surgical procedure.

Although the invention has been described with reference to particular embodiments, the description is only an example of the invention's application and should not be taken as a limitation. Various other adaptations and combinations of features of the embodiments disclosed are within the scope of the invention as defined by the following claims.

What is claimed is:

1. A teleoperational instrument system, comprising:
   a flexible tubular shaft having a proximal end and a distal end;
   a mechanism coupled to the proximal end of the flexible tubular shaft, the mechanism comprising a plurality of capstans, each capstan including:
      a bore sized for concentric engagement with a drive shaft of a respective drive motor configured to drive the capstan, and
      a capstan coupling member adapted to engage with a drive shaft coupling member such that rotation of the drive shaft causes rotation of the capstan about a drive axis concentric with the bore and the drive shaft, and further adapted to disengage from the drive shaft coupling member such that rotation of the drive shaft does not cause rotation of the capstan; and
   a plurality of tendons, each of the plurality of tendons including a proximal section coupled to one of the plurality of capstans and a distal section coupled to a member disposed at the distal end of the flexible tubular shaft.

2. The teleoperational instrument system of claim 1, wherein the capstan coupling member is a projection and the drive shaft coupling member is a slot.

3. The teleoperational instrument system of claim 1, wherein the drive shaft coupling member is a projection and the capstan coupling member is a slot.

4. The teleoperational instrument system of claim 1, wherein the plurality of capstans includes a plurality of rows of capstans.

5. The teleoperational instrument system of claim 1, wherein each capstan of the plurality of capstans has a single engaging orientation with respect to the drive shaft of the respective drive motor.

6. The teleoperational instrument system of claim 1, wherein each capstan of the plurality of capstans is arranged in parallel alignment with each of the other capstans in the plurality of capstans.

7. The teleoperational instrument system of claim 1, wherein each tendon of the plurality of tendons extends through a sheath inside the flexible tubular shaft.

8. The teleoperational instrument system of claim 1, wherein the drive axis is perpendicular to the proximal end of the flexible tubular shaft.

9. The teleoperational instrument system of claim 1, wherein the mechanism engages each respective drive motor through a sterile barrier.

10. A teleoperational instrument assembly, comprising:
a teleoperational manipulator including a plurality of drive motors;
a flexible tubular shaft having a proximal end and a distal end;
a mechanism coupled to the proximal end of the flexible tubular shaft, the mechanism comprising a plurality of capstans, each capstan including:
   a bore sized for concentric engagement with a drive shaft of a respective drive motor of the plurality of drive motors, and
   a capstan coupling member adapted to engage with a drive shaft coupling member such that rotation of the drive shaft causes rotation of the capstan about a drive axis concentric with the bore and the drive shaft, and further adapted to disengage from the drive shaft coupling member such that rotation of the drive shaft does not cause rotation of capstan; and
a plurality of tendons, each of the plurality of tendons including a proximal section coupled to one of the plurality of capstans and configured to wind around the capstan and including a distal section coupled to a member disposed at the distal end of the flexible tubular shaft.

11. The teleoperational instrument assembly of claim 10, wherein drive shafts of the plurality of drive motors extend in parallel to each other.

12. The teleoperational instrument assembly of claim 10, wherein drive shafts of the plurality of drive motors are arranged in a plurality of rows extending from a base member of the teleoperational manipulator.

13. The teleoperational instrument assembly of claim 10, wherein the capstan coupling member is a projection and the drive shaft coupling member is a slot.

14. The teleoperational instrument assembly of claim 10, wherein the drive shaft coupling member is a projection and the capstan coupling member is a slot.

15. The teleoperational instrument assembly of claim 10, wherein the plurality of capstans includes a plurality of rows of capstans.

16. The teleoperational instrument assembly of claim 10, wherein each capstan of the plurality of capstans has a single engaging orientation with respect to the respective drive shaft of the teleoperational manipulator.

17. The teleoperational instrument assembly of claim 10, wherein each capstan of the plurality of capstans is arranged in parallel alignment with each of the other capstans in the plurality of capstans.

18. The teleoperational instrument assembly of claim 10, wherein each tendon of the plurality of tendons extends through a sheath inside the tubular shaft.

19. The teleoperational instrument assembly of claim 10, wherein the drive axis is perpendicular to the proximal end of the flexible tubular shaft.

20. The teleoperational instrument assembly of claim 10, wherein the mechanism engages the plurality of drive motors through a sterile barrier.

* * * * *

UNITED STATES PATENT AND TRADEMARK OFFICE
CERTIFICATE OF CORRECTION

PATENT NO. : 10,772,690 B2  
APPLICATION NO. : 16/026673  
DATED : September 15, 2020  
INVENTOR(S) : Giuseppe M. Prisco Page 1 of 1

It is certified that error appears in the above-identified patent and that said Letters Patent is hereby corrected as shown below:

On the Title Page

Item (57), Lines 1-8, The Abstract should read as:
-- A teleoperational instrument system includes a flexible tubular shaft; a mechanism coupled to the proximal end of the flexible tubular shaft, and a plurality of tendons. The mechanism includes a plurality of capstans, each including: a bore sized for concentric engagement with a drive shaft of a respective drive motor configured to drive the capstan; and a capstan coupling member adapted to engage with a drive shaft coupling member so rotation of the drive shaft causes rotation of the capstan about a drive axis. The capstan coupling member is adapted to disengage from the drive shaft coupling member so rotation of the drive shaft does not cause rotation of the capstan. Each of the plurality of tendons includes a proximal section coupled to one of the plurality of capstans and a distal section coupled to a member disposed at the distal end of the flexible tubular shaft. --

In the Specification

Column 1, Lines 7-13, under Cross-Reference to Related Applications should read as follows:
-- This application is a continuation application of U.S. Application No. 15/001,948, filed January 20, 2016, which is a continuation application of U.S. Application No. 12/286,644, filed September 30, 2008, and issued as U.S. Pat. No. 9,259,274, on February 16, 2016, both of which are incorporated herein by reference in their entireties. --

In the Claims

Column 14, Lines 20-22, Claim 18 should read:
-- The teleoperational instrument assembly of claim 10, wherein each tendon of the plurality of tendons extends through a sheath inside the flexible tubular shaft. --

Signed and Sealed this  
Fifth Day of January, 2021

Andrei Iancu  
*Director of the United States Patent and Trademark Office*